United States Patent [19]

Stoneback

[11] 4,316,456
[45] Feb. 23, 1982

[54] SURGICAL DRAPE SYSTEM

[75] Inventor: W. Keith Stoneback, Arlington Heights, Ill.

[73] Assignee: American Hospital Supply Corporation, Evanston, Ill.

[21] Appl. No.: 115,585

[22] Filed: Jan. 25, 1980

[51] Int. Cl.³ .............................................. A61F 13/00
[52] U.S. Cl. ................................................. 128/132 D
[58] Field of Search ................... 128/132 D, 155, 156, 128/292, 157

[56] References Cited

U.S. PATENT DOCUMENTS

| Re. 27,710 | 7/1973 | Melges | 128/132 D |
|---|---|---|---|
| 3,721,234 | 3/1973 | Hadtke et al. | 128/132 D |
| 3,799,161 | 3/1974 | Collins | 128/132 D |
| 3,871,369 | 3/1975 | Krzewinski | 128/132 D |
| 3,881,474 | 5/1975 | Krzewinski et al. | 128/132 D |
| 3,882,859 | 5/1975 | Ericson | 128/132 D |
| 3,916,887 | 11/1975 | Kelly | 128/132 D |
| 3,923,052 | 12/1975 | Zoephel | 128/132 D |
| 4,024,862 | 5/1977 | Collins | 128/132 D |
| 4,041,942 | 8/1977 | Dougan et al. | 128/132 D |
| 4,089,331 | 5/1978 | Hartigan et al. | 128/132 D |

*Primary Examiner*—John D. Yasko
*Attorney, Agent, or Firm*—Larry Barger; Mary Jo Kanady

[57] ABSTRACT

A surgical drape system that includes a small bottom drape with a fenestration and adhesive means to secure the bottom drape to a patient. The system also includes a top drape with an opening that is substantially larger than the bottom drape's fenestration, but which is smaller than the bottom drape itself. The bottom drape, which is immediate the surgical wound, is of a more liquid repellent material, while the top drape is of a softer, more drapeable material.

11 Claims, 5 Drawing Figures

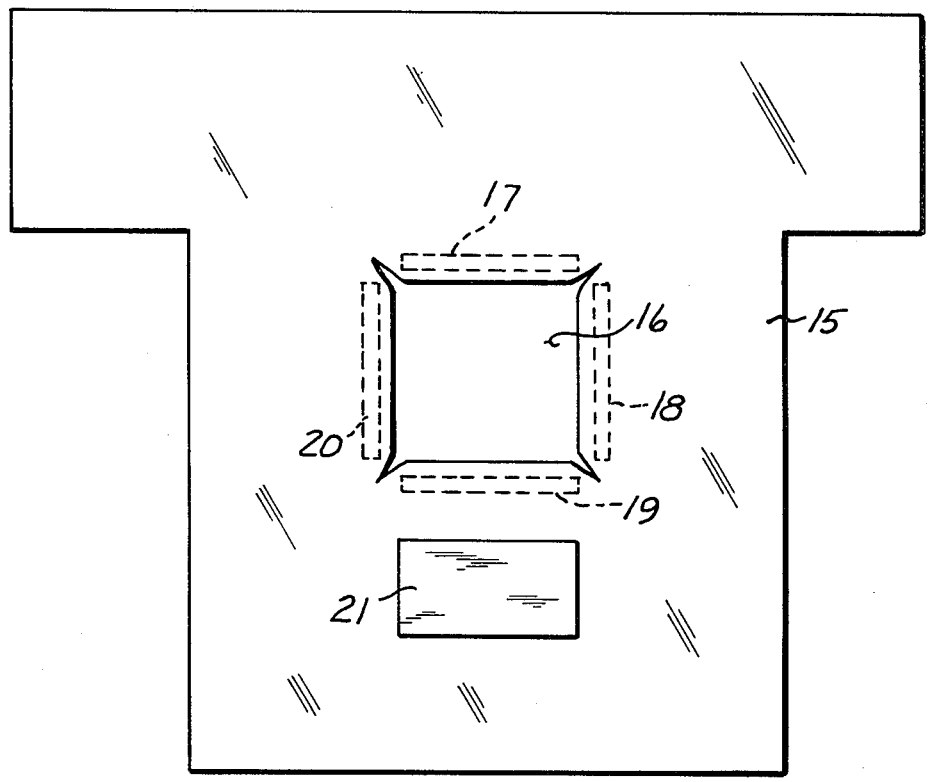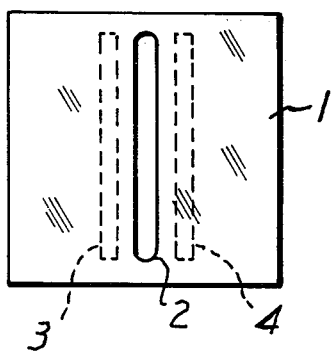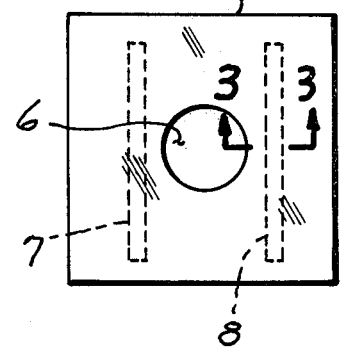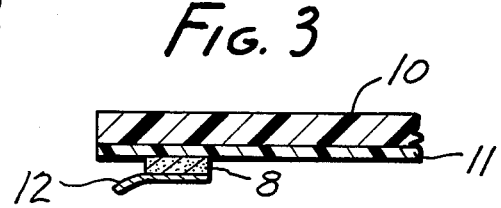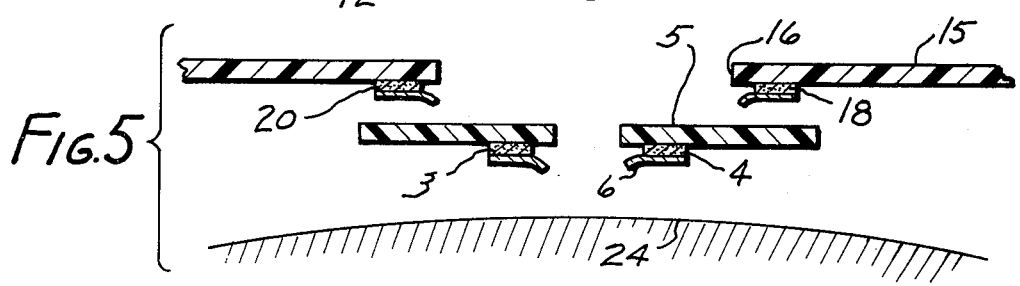

SURGICAL DRAPE SYSTEM

BACKGROUND

Disposable, fenestrated surgical drapes are well-known in the medical industry. An example is U.S. Pat. No. 4,401,942.

These fenestrated drapes are often quite large in size so as to completely cover the patient and drape down the sides of the operating table to prevent bacterial contamination of the patient. Because of the numerous sizes and shapes of fenestrations needed for different types of surgical procedures, a hospital must stock a tremendous amount of surgical drapes.

Most fenestrated drapes in the past have been made of a single material so that the highly repellent material adjacent the fenestration was used throughout the entire drape, including those portions hanging down the sides of the operating room table. The liquid repellent coating or laminated sheet on the drape material that hung down from the sides of the operating room table caused it to be stiffer and less drapeable than desired. Also, it increased the cost of the total drape to make it entirely liquid repellent in order to get the liquid repellency adjacent the fenestration.

U.S. Pat. No. 3,882,859 has proposed permanently securing a rubber sheet across a very large opening of a surgical drape. The rubber sheet is then split for the surgical incision. However, the rubber sheet does not have a preshaped fenestration. It is simply cut at the time of surgery.

Another U.S. Pat. No. 4,024,862 has a series of smaller drapes on top of a main drape. Each smaller drape has progressively larger fenestrations. Thus, during a surgical procedure if a larger fenestration is needed, the top drape is simply peeled off and discarded. However, since all drapes are preassembled by the manufacturer, this does not solve the large inventory problem required to get a specific drape with an oval fenestration, as shown in 39' in FIG. 9. The purpose of this patent is simply to provide a drape that does not need to be cut during surgery to enlarge the fenestration.

SUMMARY OF THE INVENTION

The present invention overcomes the inventory problems, and also provides an improved drapeability to the side areas of a drape hanging over the edges of the operating room table. This invention includes a draping system with a separate bottom drape having a fenestration of the particular size and shape for the surgery. This bottom drape is of a highly liquid repellent material, and preferably is adhesively secured directly to the patient. A separate top drape of this draping system has an opening larger than the bottom drape's fenestration, but smaller than the entire bottom drape. The top drape is adhesively secured in superimposed relationship over the bottom drape. Preferably the top drape, which is adapted to hang over edges of the operating room table, is of a softer, more drapeable material, which can be less liquid repellent than the bottom drape.

RELATED APPLICATION

Method of Draping A Surgical Patient, filed Jan. 25, 1980, Ser. No. 115,471, by W. Keith Stoneback.

THE DRAWINGS

FIG. 1 is a top plan view of a first bottom drape with an elongated fenestration;

FIG. 2 is a top plan view of a second bottom drape with a different circular fenestration;

FIG. 3 is an enlarged sectional view taken along line 3—3 of FIG. 1;

FIG. 4 is a top plan view of a top drape; and

FIG. 5 is an exploded view showing the relationship between the top and bottom drapes and the patient.

DETAILED DESCRIPTION

In FIG. 1, a first embodiment of a bottom drape 1 is shown. This drape has an elongated fenestration 2 and a pair of adhesive strip members 3 and 4 adjacent fenestration 2.

A second embodiment of a bottom drape 5 is shown in FIG. 2, and this bottom drape has a fenestration 6 that is of a circular shape. Also, in the bottom of drape 5 is a pair of adhesive members 7 and 8 adjacent fenestration 6. In the FIG. 3 section, the drape is shown as composed of a main body 10 which can be of a nonwoven, cellulosic material. A bottom surface of the main body 10 is preferably laminated to a liquid repellent layer 11. Layer 11 can be a liquid repellent coating or a separate thermoplastic film bonded to the main body 10 of bottom drape 5.

Because of the liquid repellent nature of the bottom drape, it tends to become stiffer than desired for a complete drape. However, the liquid repellency is needed in the very close proximity to the surgical incision. This bottom drape is secured at the incision site by the adhesive 8 which has a tear off protective liner 12 that is removed immediately prior to sticking the adhesive 8 directly to the patient's skin.

After either bottom drape 1 or bottom drape 5 has been secured to the patient, a top drape 15, which is much larger than the bottom drape, can have any desired configuration, as shown in FIG. 4. Here the top drape is illustrated as having a generally T-shape. The top drape has a large opening 16 which is shown with cut or notched corners defining flaps which have adhesive strips 17, 18, 19 and 20 on their bottom surfaces. These adhesive strips are similar to those shown in FIG. 3 with a protective liner. The top drape can also include a slip resistant pad, such as a rubber sheet 21, for laying surgical instruments on during an operation.

As shown in the exploded view of FIG. 5, the top drape 15 is superimposed on bottom drape 5, and secured to the bottom drape by adhesive strips 17, 18, 19 and 20. The bottom drape 5 can be of a more liquid repellent material even though such liquid repellent material may have a more stiff, paper-like characteristic that is undesirable for an entire surgical drape. The top drape, since it is protected from the surgical site by the bottom drape, can be of a softer, more drapeable, cloth-like material, such as a nonwoven, cellulosic material having less liquid repellent characteristics. The outer drape can thus more readily drape and follow the contours of the patient, operating room table, etc. as would a cloth drape. Also, the top drape can be made of a less expensive material which need not have all of the liquid repellent characteristics, etc. Also, if desired, the more critical bottom drape can have additional bactericidal agents, etc. that may not be required with the top drape. In short, two separate materials can be used for the bottom and top drape.

Also of great importance is the hospital inventory problem that is greatly reduced with the present invention. For instance, the hospital can stock only a variety of the small bottom drapes with different sizes and shapes of fenestrations. The hospital can stock only a standardized top sheet which can be used with many different bottom sheets having different sizes and shapes of fenestrations. Once the bottom and top drape are combined at the patient's site, they have the effect of a single drape having the desired fenestration. Thus, a hospital need not stock a a large number of complete drapes which may be in the order of 6'×10' simply to get the different sizes and shapes of fenestration needed for the various surgical procedures.

In the foregoing description, specific examples have been used to describe the invention. However, it is understood by those skilled in the art that certain modifications can be made to these examples without departing from the spirit and scope of the invention.

I claim:

1. A surgical drape system comprising a plurality of bottom drapes having different fenestrations; a top drape with an opening smaller than the bottom drape, but larger than the bottom drape's fenestration; and the system includes means to secure the bottom drape to a patient and the top drape in superimposed position on the bottom drape, whereby the top drape can be coupled with one of a plurality of bottom drapes to provide a drape system with the desired fenestrations.

2. A surgical drape system as set forth in claim 1, wherein the bottom drape has securing means for attaching the bottom drape to a patient.

3. A surgical drape system as set forth in claim 1, wherein the top drape has securing means for attaching the top drape to the bottom drape.

4. A surgical drape system as set forth in claim 1, wherein the bottom drape has a greater liquid repellency than the top drape.

5. A surgical drape system as set forth in claim 4, wherein the bottom drape has a liquid repellent layer on its bottom surface.

6. A surgical drape system as set forth in claim 5, wherein the layer is a polyolefin.

7. A surgical drape system as set forth in claim 1, wherein the top drape has greater drapeability than the bottom drape.

8. A surgical drape system as set forth in claim 7, wherein the top drape is of a nonwoven material.

9. A surgical drape system as set forth in claim 1, wherein the top drape has a slip resistant panel for holding medical instruments.

10. A surgical drape system as set forth in claim 1, wherein the top drape has an adhesive means on its undersurface for securement to the bottom drape.

11. A surgical drape system as set forth in claim 1, wherein the bottom drape has adhesive means on its undersurface for securement to a patient.

* * * * *